United States Patent [19]

Klett

[11] Patent Number: 4,495,952

[45] Date of Patent: Jan. 29, 1985

[54] APPARATUS FOR MEASURING JAW MOVEMENT

[76] Inventor: Rolf Klett, Nikolaushöhe 15a, D-8702 Gerbrunn, Fed. Rep. of Germany

[21] Appl. No.: 371,578

[22] Filed: Apr. 26, 1982

[30] Foreign Application Priority Data

Apr. 30, 1981 [DE] Fed. Rep. of Germany ....... 3117174
Jul. 8, 1981 [DE] Fed. Rep. of Germany ....... 3126911

[51] Int. Cl.³ ............................................. A61B 5/10
[52] U.S. Cl. ................................. 128/777; 33/125 A; 356/373; 433/69
[58] Field of Search .................... 433/68, 69; 128/777, 128/774, 782, 776; 250/231 R; 356/373, 375; 33/125 A

[56] References Cited

U.S. PATENT DOCUMENTS

| 3,784,309 | 1/1974 | Brelot et al. | 33/125 A X |
| 4,249,076 | 2/1981 | Bergstrom et al. | 250/231 R X |
| 4,275,393 | 6/1981 | Johnston | 250/231 R X |
| 4,358,960 | 11/1982 | Porter | 250/231 R X |

FOREIGN PATENT DOCUMENTS

| 2825204 | 12/1979 | Fed. Rep. of Germany | 433/69 |
| 215403 | 6/1968 | U.S.S.R. | 128/777 |
| 232447 | 10/1969 | U.S.S.R. | 128/777 |

OTHER PUBLICATIONS

"Photoelectric Mandibulography: A Technique for Studying Jaw Movements", Barrie R. D. Gillings, *J. Pros. Dent.*, pp. 109–121; Feb., 1967.
"Investigation of Functional Mandibular Movements; Theodore Messerman et al., *Dental Clinics of North America*, pp. 629–642; Jul., 1969.
"A Digital Optoelectronic Method for Recording Mandibular Movement in Association with Oral Electromyograms and Temporomandibular Joint Noises" A. J. Duxbury et al; *Medical and Biological Engineering*", pp. 707–711; Sep., 1974.

Primary Examiner—Kyle L. Howell
Assistant Examiner—John C. Hanley
Attorney, Agent, or Firm—Lane, Aitken & Kananen

[57] ABSTRACT

An apparatus for the contactless measuring of the movement in three dimensions of the jaw and of the condyle in the temporo-mandibular joint respectively comprising opto-electronic signal transmitters and signal receivers between which light signals are transmitted. In one embodiment, a measuring head having light transmitters and light receivers mounted therein is secured to the lower jaw and moves with the lower jaw relative to reflecting plates. The light receivers generate signals varying with the length of the light path between the transmitter and the receiver and thus represent the movement of the lower jaw. In a second embodiment, the light transmitters generate collimated beams of light and are fixed to move with the lower jaw with respect to light receivers which have biaxial position sensitivity to the transmitted light beams. In a third embodiment, light beam transmitters are moved with the lower jaw relative to gratings so as to generate light pulses corresponding to movement of the lower jaw.

9 Claims, 10 Drawing Figures

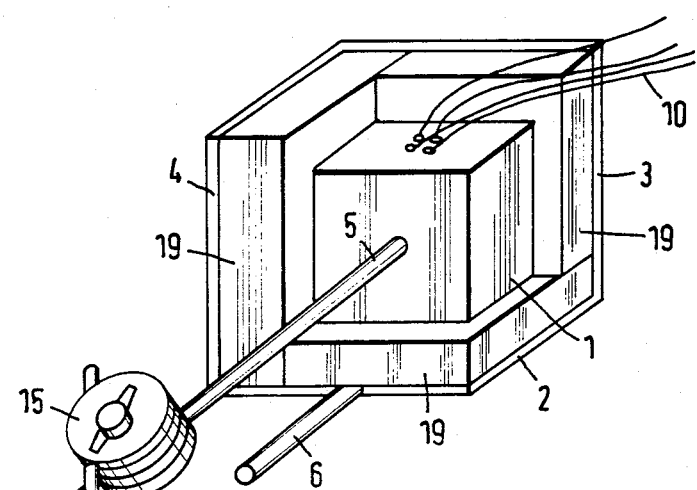
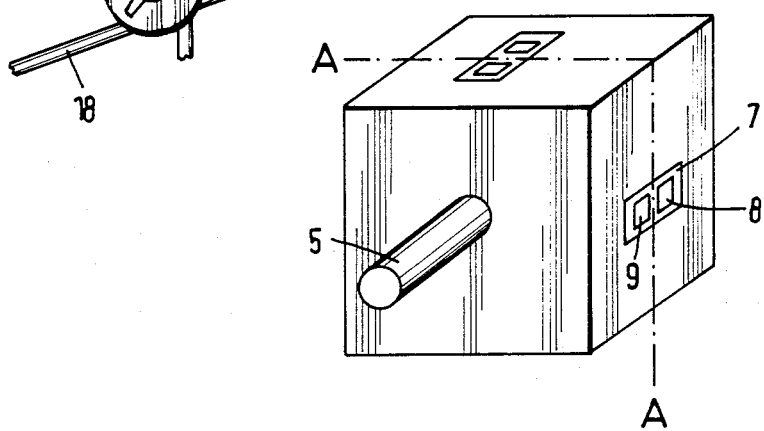

APPARATUS FOR MEASURING JAW MOVEMENT

BACKGROUND OF THE INVENTION

The invention relates to an apparatus for the contactless measuring of movement in one to three dimensions of the jaw and of the condyle in temporo-mandibular joint, respectively, by means of measuring devices comprising optoelectronic signal transmitters and signal receivers, between which light signals are transmitted either directly or by reflectors, part of the measuring device being secured to the lower jaw of the patient.

Prior to the present invention, optoelectronic devices for measuring the movement of the jaw were known. One such device is disclosed in the German published patent application, Offenlegungsschrift DE-OS No. 28 25 204 (page 12, lines 9 through 14). The signal receivers (sensors) of the apparatus disclosed in this patent application are mounted on a plate arranged in a plane and comprise a plurality of phototransistors which are interconnected electrically. The light sources of the apparatus are light signal transmitters such as light-emitting diodes. This apparatus allows measuring in each dimension because the integral signal received by the phototransistors depends on the distance between the phototransistors and the light source. The drawback of this system is that the measuring signal can easily be invalidated by unwanted light, especially when the distances between the light signal transmitter and signal receiver are great, and that there is no linearity between the generated output signal and distance between signal transmitter and signal receiver. A linear output can be achieved by means of electronic correction circuits but only at great expense and even then only approximately. Moreover, the arrangement of the plates with many signal receivers in combination with the signal transmitters are relatively complicated. The large number of receivers must be arranged on an expanded area and must be connected in parallel so that the integral received signal is responsive only to the distance between transmitter surface and receiver surface and not also additionally responsive—due to marginal zone effects—to the transverse displacement of the signal transmitter (and reflector, respectively) relative to the receiver surface whereby the measured result responsive to the distance would be invalid. As condyle movements in the temporo-mandibular joint into different directions are possible within the range of about 2 cm, the receiving surfaces must be large and must contain a large number of equivalent receivers in order to achieve homogeneity of reception sensitivity over the total area of motion and beyond. If independence on the transverse displacements over the total area of motion is to be achieved, receivers must be provided far outside the area of motion where the light intensity is still measurable. Otherwise, marginal distortions invalidate the measured result.

In FIG. 4 of the above-mentioned published German patent application, the measuring head opposite the plates carrying light signal transmitters and receivers is ball-shaped and has an overall reflecting surface so that rotations of the reflector do not affect the measured result. According to the patent application disclosure, many transmitters and receivers are distributed on a large surface and connected in parallel in order to make the output signal independent of the transverse displacement of the reflector relative to the measured surface. This measuring device is very complicated and expensive. If the technical problems are to be reduced reducing the number of signal transmitter and receiver units, a restricted measuring surface and a measurement signal distorted by marginal effects is the necessary result.

The principle that the output of a photocell is a measure of the distance between a light source and photocell is described in J. Pros. Dent. Vol. 17, February 1967, pp. 109–121. As described in this article, several photocells are arranged side by side and connected parallel (cf. FIGS. 3 and 4 on page 111 and page 113, and the corresponding text) so that the output signal is not changed when the light source moves on a line maintaining equal distance from the photocells.

In Dental Clinics of North America, 13, 1969, pp. 629 to 642, a measuring device is described wherein six incremental transducers are provided as units (pp. 631 and 632). In each incremental transducer, a grating is moved between light emitting diodes and photocells, the movement of the grating being effected mechanically. The mounting ends of each incremental transducer are mechanically connected to the two face bows secured to upper and lower jaw. Because of this connection and the mechanical guide of the grating, the movement of the upper and lower jaw is not free of forces. Accordingly, an undisturbed recording of the movement of the lower jaw, which is controlled by sensitive neuromuscular reflexes and which is important for the temporo-mandibular joint diagnostics (TMJ-diagnostics), is impossible. Moreover, the signal received from each transducer is not a direct measure for the diagnostically important movement of the condyle in the temporo-mandibular joint in a given dimension, because each transducer measures, at a position far away from the temporo-mandibular joint, only the distance between the mounting points of the transducer at the two face bows when the lower jaw moves. A movement at the location of the joint can be determined only by a complicated calculation because of the mechanics of the rigid body.

The problem underlying the invention was to develop an apparatus of the type described above which has a simple construction and wherein the requirements on the evaluation circuit are not too severe and which delivers output quantities which are a direct measure of the movement of the jaw and of the condyle in the temporo-mandibular joint, respectively.

SUMMARY OF THE INVENTION

The first described embodiment of the invention has the advantage that for each measurement plane only one signal transmitter and one signal receiver is required and, thus, a simple construction is guaranteed. By arranging the transmitter and receiver directly side by side and by facing a planar reflector, independence of the measured signal from the transverse displacement is achieved because the conditions of reflection upon transverse movement do not vary and because only the light beams reflecting back on themselves reach the receiver and are measured. Even slight rotations of the reflector will not cause an interfering influence if the light of the transmitter is not greatly focused. Furthermore, the device has a special advantage of permitting quick and safe spatial adjustment of the measuring head because self-centering is effected by inserting the measuring head into the reflectors equipped with spacer plates and arranged complementarily to the measuring head. Fixing the position of the measuring head and of the reflectors is effected by arresting the position of swivel joints. This process takes only a few seconds. For a quick zero setting (basic distance) spacers of selectable thickness are inserted between the reflecting surfaces of the measuring plates and the measuring head. As a result of the precisely definable basic distance, the linearity of the apparatus is maintained to a high degree.

In another embodiment of the invention for the contactless measuring of movements in three dimensions of the jaw and of the condyle in the temporo-mandibular joint, a signal receiver with position sensitivity transverse to the impact direction of the light beam is employed.

This embodiment of the invention has several advantages. A conventional uniaxial or biaxial position-sensitive signal receiver may be used having the usual existing linearity between the position displacement of an impinging light beam and the output signal resulting in the advantage that a very good linearity is achieved between measurement signal and relative movement of the signal receiver transverse to the light beam without recourse to complicated and expensive circuitry in that an electronic linearization circuit is not required. The range of linearity reaches up to a few centimeters. Larger ranges of linearity are not necessary for the diagnosis of movement of the condyle and of the jaw, respectively. The high resolving power achieved is better than 10 μm. The output signal is not influenced disadvantageously by variations in the distance between light source and signal receiver. A special advantage in the use of a biaxial position-sensitive signal receiver is that by means of one transmitter and one receiver a precise and uncomplicated measurement in two dimensions is possible and that the output signals of the signal receiver are a direct measure of the movement in the respective dimensions. With conventional position-sensitive signal receivers, an effective stray light compensation can be performed relatively simply by means of known circuit techniques.

Very good linearity and high resolving power can be achieved with the apparatus also by using quadrant photodetectors or continuously measuring linear position-sensitive diodes with uniaxial or biaxial position sensitivity, the analog output signals of which are proportional to the position displacements of the impact light beam.

For digital measured value detection, charge displacement devices, e.g. charge-coupled devices (CCD) are especially advantageous. Such devices are divided into miniature discrete photosensitive surface elements (about 10 μm×10 μm). The output signals from such devices are processed like output signals from picture sensors and are available in digital form, which simplifies the processing of signals by means of computers.

According to a third embodiment of the invention, the lines of a grating are scanned optically transverse to the direction of the lines and are counted. An essential fact is that no power is transmitted directly or indirectly between signal transmitters and gratings. The number of the received pulses is a direct measure for the movement of the jaw in a direction transverse to the grating. The advantage of this solution is the linearity is defined by the quality of the grating and the fact that the signals are digital and can be processed immediately in computers or counters. When coded gratings are used, absolute position measurement can be performed advantageously.

For generating a focused light beam, light-emitting diodes with narrow radiation characteristic are preferably used. Their emitted light can be better focused by lens systems. Best results with respect to the resolving power can be achieved by the use of lasers (e.g. of the helium-neon type) since they emit a collimated light beam. The danger of eye injury can be avoided by shielding.

The different apparatus for the contactless measuring of movements of the jaw and of the condyle in the temporomandibular joint can easily be combined with conventional pantographs operating with writing boards and styli as they are used in gnathologic dentist's practices. Such complicated mechanical devices are very expensive and can be upgraded economically to highly precise instruments by the measuring device of the invention. A special advantage is also that the handling of the apparatus learned in expensive training need not be changed considerably. The adjusting process is rather simplified with substantially increased measurement information.

BRIEF DESCRIPTION OF THE DRAWINGS

FIG. 1 a perspective view of one embodiment of the measuring apparatus of the invention;

FIG. 2 is a perspective view of the measuring head of the apparatus shown in FIG. 1, the measuring head being turned 180° relative to its working position;

DESCRIPTION OF THE PREFERRED EMBODIMENTS

Figure 3:
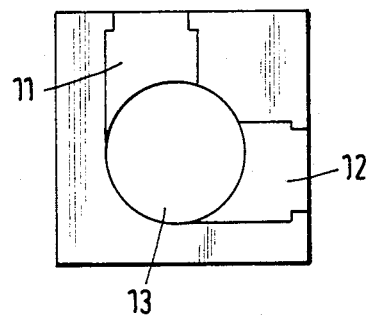
FIG. 3 is a view of a section through the measuring head shown in FIG. 2 along the plane A—A.

The measuring device illustrated in FIG. 1 comprises a measuring head 1 coacting with orthogonally arranged measuring plates 2, 3, and 4. The measuring head 1 is mounted on a single arm 5 which is connected by two swivel joints 15 and 16 and one intermediate rod 17 to the transverse rod 18 of a pantograph secured to the lower jaw of a patient. The measuring plates 2, 3, and 4 are interconnected and are mounted on an arm 6 which is connected by rods of the pantograph to the upper jaw of the patient. The surfaces of the supporting plates 2, 3, and 4 facing the measuring head have optically reflecting surfaces. The measuring head 1 is provided with three orthogonal surfaces, facing the reflecting surfaces of the supporting plates 2, 3, and 4. In these surfaces of the measuring head opposite the reflecting surfaces of the measuring plates 2, 3, and 4, intergrated optical transmitter and receiver units 7 (see FIG. 2) are mounted. Each transmitter and receiver unit comprises a light transmitter 8 and light receiver 9 and is positioned such that the light emitted by the transmitter 8 is reflected by the opposite reflection surface to the corresponding receiver 9. The transmitter 8, for instance, may be a light-emitting diode. The receiver 9, for instance, may be a photo-transistor, the output current of which will depend on the length of the light path between transmitter and receiver. The leads 10 at the upper end of the measuring head 1 electrically connect the transmitter 8 and receiver 9 of each transmitter and receiver unit to an evaluation circuit.

For initial adjustment, the cube shaped measuring head 1 is inserted into the arrangement comprising the three orthogonally arranged measuring plates 2, 3, and 4. The resulting position of the measuring head 1 relative to the reflection surfaces of the measuring plates 2, 3, and 4 is fixed with respect to the transverse rod 18. This is done by simply arresting the swivel joints 15 is a fixed position.

In order to precisely position the head 1 at the beginning of the measurement, spacer plates 19 of a selectable thickness are inserted for adjustment between the reflecting surfaces and the measuring head and are withdrawn after arrest of the swivel joints 15 and 16. The measuring plates are aligned with respect to the axis of rotation of the temporo-mandibular joint wherein one plate is in or parallel to the horizontal plane of the cranium, one plate is in or parallel to the front plane of the cranium and one plate is in or parallel to the sagittal plane of the cranium. The horizontal plane of the cranium is a plane which is horizontal when the head is in a normal upright position and the front plane of the cranium is a plane which is vertical and parallel to the face when the head is in the normal upright position. After adjustment, the measuring process can then be performed immediately.

The measuring head is adapted to be inclined with respect to the reflection surfaces by several angular degrees without the output signal changing.

By means of the above described measuring device, the relative movement between the lower and upper jaw can be measured.

The measuring device according to the invention can be used in a simple manner in combination with the usual pantographs operating with writing boards and styli, the measuring device being secured to the rods of the pantograph in place of the normal writing board and the styli. The resolving power achieved by the measuring device according to the invention of about 10 μm is substantially higher than the accuracy that can be achieved by means of the writing boards or styli.

FIG. 2 shows the arrangement of the integrated transmitter and receiver units 7 in the head 1, each with a transmitter 8 and receiver 9.

The sectional view shown in FIG. 3 taken along the sectional plane A—A of FIG. 2 shows that the measuring head 1 is provided with recesses 11 and 12 in which transmitter and receiver units 7 are inserted. In the middle of the measuring head 1, a recess 13 is provided through which the leads 10 extend.

Figure 4:
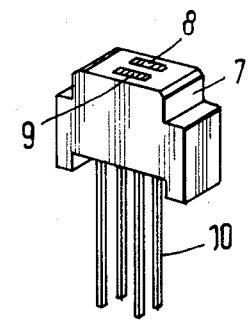
FIG. 4 is a perspective view of an integrated signal emitting and signal receiving unit used in a measuring head shown in FIGS. 2 and 3.

An integrated transmitter and receiver unit 7, as used in the measuring head of FIGS. 2 and 3, is illustrated in FIG. 4. As shown, the transmitter 8 is arranged directly beside the receiver 9. The leads 10 extend from the opposite side of the unit.

Figure 5:
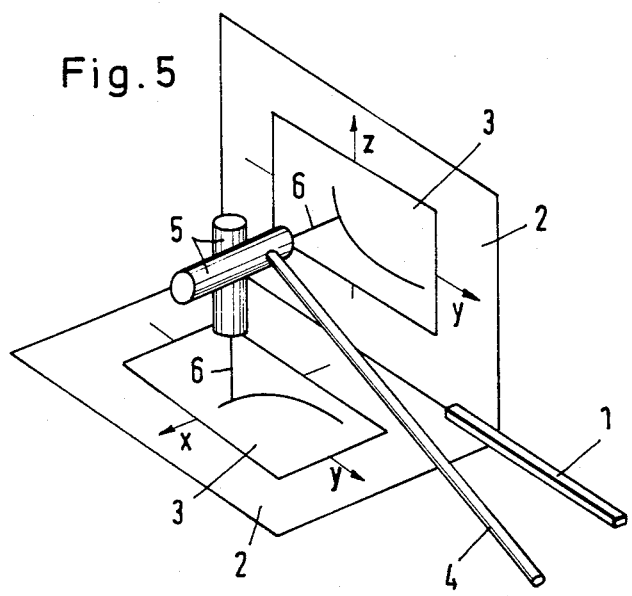
FIG. 5 is a perspective view of another embodiment of the invention for the contactless measurement of the movement of the condyle and the jaw, respectively, in three dimensions by means of biaxial position-sensitive photodetectors.

The embodiment of the invention illustrated in FIG. 5 like that of FIG. 1 is for the contactless measuring in three dimensions of movements of the jaw or the condyle in the temporomandibular joint. As shown in FIG. 5, the device comprises a rod 21 adapted to be connected to the upper jaw. Two vertically arranged support members 22 are secured to the rod 21. A photo-sensitive signal receiver 23 with biaxial position sensitivity is mounted on each of said support members. The signal receivers with biaxial position sensitivity each emit separate signals representing displacement in two directions, namely x and y and z and y, respectively, for evaluation in an evaluation circuit. A bar 24 is adapted to be secured to the lower jaw and signal transmitters 25 are mounted on the bar 24. As in the embodiment of FIG. 1, the transmitters may be light-emitting diodes arranged to generate a light beam or, alternatively, may be lasers. Each signal transmitter 25 emits a focused light beam 26 impinging perpendicularly on the photosensitive signal receivers 23. When the lower jaw is moved or turned relative to the upper jaw, the corresponding position change of the signal transmitter transversely to the direction of the light beam is detected by the signal receivers and the respective signal receiver emits an x-signal and a y-signal or a y-signal and a z-signal.

Figure 6:
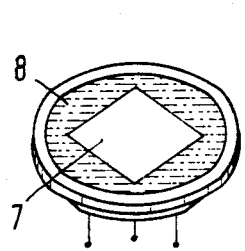
FIG. 6 is a perspective view of a biaxial linear position-sensitive diode employed as a photo-sensitive signal receiver in the device shown in FIG. 5.

FIG. 6 shows a perspective view of a biaxial linear position-sensitive diode from above. It shows the square position-sensitive field 27 within the background surface 28.

Figure 7:
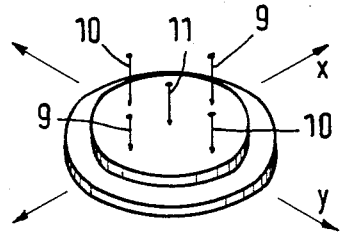
FIG. 7 is a perspective view of the diode of FIG. 6 shown from below.

FIG. 7 shows the connection side of the biaxial linear position-sensitive diode. It is provided with two pairs of terminals 29 and 30 each for the two orthogonally arranged directions of the axes. The central terminal 31 is used for voltage supply.

Figure 8:
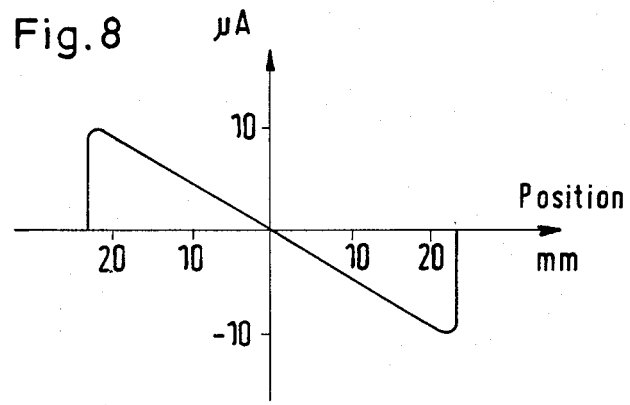
FIG. 8 shows the transmission function of the position-sensitive diode shown in FIGS. 6 and 7 along one axis.

FIG. 8 illustrates the transmission function of a linear position-sensitive diode for displacement along one axis, the function being identical for displacement along the other axis. As shown, the transmission function is linear for a wide area of the position displacement of the impinging light beam. In this way, an exact measurement can be performed with two biaxial linear position-sensitive diodes by means of a device as shown in FIG. 5.

Figure 9:
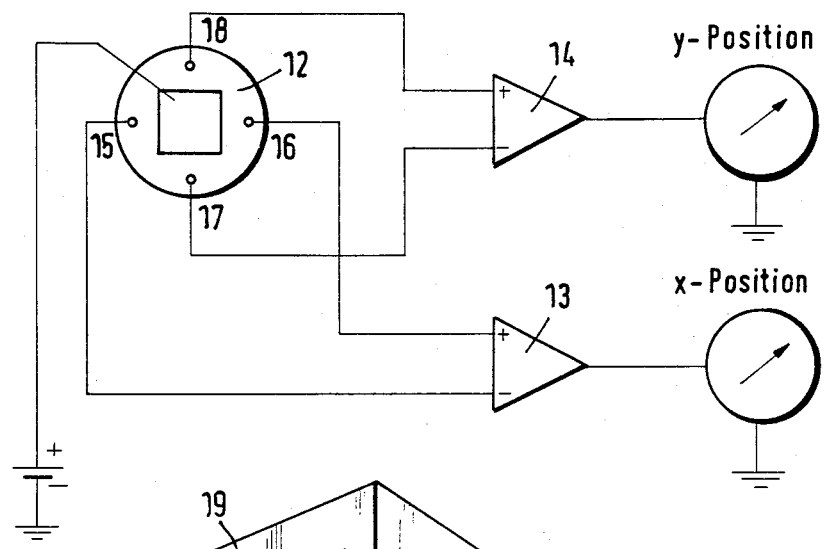
FIG. 9 is a basic circuit diagram for evaluation of the signals emitted by a photo-sensitive signal receiver with biaxial position sensitivity for use with the device shown in FIG. 5.

FIG. 9 illustrates a basic circuit diagram for evaluating the output signals of a biaxial linear position-sensitive diode. The circuit is provided with a linear biaxial position-sensitive diode 32 having terminals 35 and 36 for the x-direction and terminals 37 and 38 for the y-direction. The terminals 35 and 36 are connected to a differential amplifier 33 and the terminals 37 and 38 are connected to a differential amplifier 34. The x-position signal results directly from the difference between the currents at the terminals 35 and 36, and the Y-position signal results directly from the difference between the currents at the terminals 37 and 38. The output signals can be displayed or processed further by means of a computer.

The receivers 23 alternatively may be charge displacement devices, e.g. charge-coupled devices. When the receivers are charge-coupled devices, the sensitive surfaces of the receivers 23 are divided into miniature discrete photo-sensitive surface elements of about 10 μm by 10 μm in size. The output signal s from such devices are then processed like the output signals from picture sensors and are available in digital form which simplifies the processing of the signals by means of computers.

Figure 10:
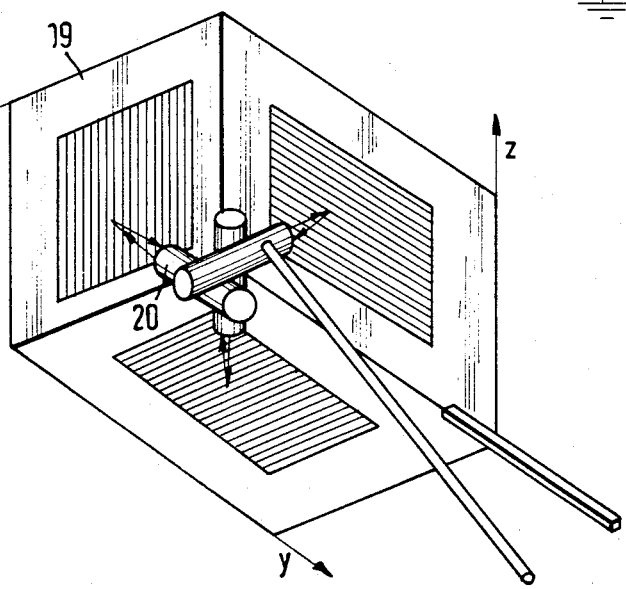
FIG. 10 is a perspective view of another embodiment of the invention for the contactless three-dimensional incremental measurement of movements of the jaw and the condyle in the temporo-mandibular joint.

The embodiment shown in FIG. 10 comprises line gratings 39 in three orthogonally arranged planes. Transmitters of the measuring head 40 transmit light beams perpendicularly to the gratings which light beams are reflected by the gratings to the receiver in the measuring head 40 so that signal pulses are produced as the transmitter moves in a direction transverse to the grating. The number of pulses produced by a grating is a direct measurement of the motion of the transmitter. The resulting pulses produced by the receivers may be counted by counters or processed directly by a computer. In this device, the gratings are connected to the upper jaw and the measuring head is connected to the lower jaw. Instead of mounting the receivers in the measuring head to receive reflected light from the gratings, the receivers may be positioned on the opposite side of the grating to receive light pulses transmitted through the gratings.

As can be appreciated by those skilled in the art, various changes and modifications may be made to the above-described embodiments of the invention without departing from the spirit and scope of the invention, which is expressed in the appended claims.

What is claimed is:

1. In an apparatus for the contactless measuring of movements of the jaw and of the condyle in the temporo-mandibular joint, respectively, comprising:
   optoelectronic signal transmitters and signal receivers, between which light signals are transmitted, part of the apparatus being adapted to be secured to the lower jaw of the patient;
   the improvement wherein the apparatus comprises a measuring head mounting said transmitters and receivers, measuring plates extending in three intersecting planes each having a reflecting surface positioned facing said measuring head;
   said transmitters and receivers comprising for each orthogonal direction a light transmitting means and a light receiving means mounted on said head adjacent to each other opposite each reflecting surface and positioned so that the light transmitted by the transmitting means and reflected by the facing reflecting surface is received by the receiving means.

2. An apparatus according to claim 1 wherein:
   each transmitter and each receiver are inserted side by side in said measuring head.

3. An apparatus according to claim 2 wherein:
   the transmitter and the receiver are integrated components.

4. An apparatus according to claim 1, characterized in:
   that the measuring head has a cube shape.

5. An apparatus according to claim 4, further comprising:
   spacer plates of selectable thickness adapted to be positioned in engagement with and between the reflecting surfaces and the surfaces of the measuring head.

6. An apparatus according to claim 1, wherein:
   the transmitters are light-emitting diodes, and the receivers are photo-transistors.

7. An apparatus according to claim 1 or claim 5, wherein:
   the measuring head and the measuring plates are mounted by means of swivel joints.

8. An apparatus according to claim 1 wherein the reflecting surfaces on said measuring plates comprise gratings arranged so that light pulses are reflected by each of said gratings, the number of the light pulses depending upon the relative movement between the measuring head and such grating transverse to the direction of the light beam.

9. An apparatus according to one of claims 1, 2 through 5 or 8 wherein said transmitting means are lasers.

* * * * *